United States Patent [19]

Merger et al.

[11] Patent Number: 4,552,985
[45] Date of Patent: Nov. 12, 1985

[54] PREPARATION OF ALDOLS

[75] Inventors: Franz Merger, Frankenthal; Peter Hettinger, Edingen-Neckarhausen; Arno Lange, Bad Durkheim, all of Fed. Rep. of Germany

[73] Assignee: BASF Aktiengesellschaft, Fed. Rep. of Germany

[21] Appl. No.: 620,558

[22] Filed: Jun. 14, 1984

[30] Foreign Application Priority Data

Jun. 15, 1983 [DE] Fed. Rep. of Germany ....... 3321517

[51] Int. Cl.$^4$ .............................................. C07C 47/19
[52] U.S. Cl. ................................... 568/497; 568/463; 568/464
[58] Field of Search ........................ 568/464, 497, 463

[56] References Cited

U.S. PATENT DOCUMENTS

| | | | |
|---|---|---|---|
| 3,135,808 | 6/1964 | Robeson et al. | 568/464 |
| 3,876,706 | 4/1975 | Levanevsky | 568/464 |
| 4,036,888 | 7/1977 | Couder et al. | 568/464 |
| 4,122,290 | 10/1978 | Immel et al. | 568/497 |
| 4,233,247 | 11/1980 | Immel et al. | 568/497 |
| 4,247,485 | 1/1981 | Immel et al. | 568/497 |
| 4,408,079 | 10/1983 | Merger et al. | 568/463 |

FOREIGN PATENT DOCUMENTS

| | | | |
|---|---|---|---|
| 739364 | 3/1970 | Belgium | 568/464 |
| 1044694 | 11/1953 | France | 568/464 |
| 2385670 | 3/1978 | France | 568/464 |
| 100015 | 1/1973 | Japan | 568/464 |

OTHER PUBLICATIONS

Bertilskold et al., "Acta Chemica Scand.", vol. 25, (1971), pp. 2211–2216.

Primary Examiner—Werren B. Lone
Attorney, Agent, or Firm—Keil & Weinkauf

[57] ABSTRACT

Novel ether-aldols of the general formula (I)

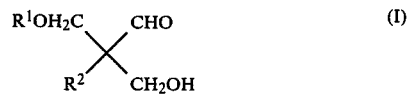

where $R^1$ and $R^2$ are each alkyl, can be prepared by reacting a 2-alkylacrolein ($H_2C=CHR^2$—CHO), an alcohol ($R^1OH$) and formaldehyde, preferably aqueous formaldehyde, in the presence of a tertiary amine.

4 Claims, No Drawings

PREPARATION OF ALDOLS

Ether-malonic acids of the general formula (II)

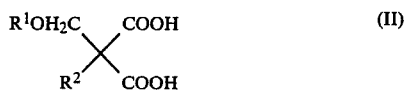

where $R^1$ is a straight-chain or branched alkyl radical of not more than 5 carbon atoms and $R^2$ is a straight-chain or branched alkyl radical of not more than 6 carbon atoms, are intermediates for important crop protection agents, and the preparation of these acids requires the corresponding aldols of the general formula (I)

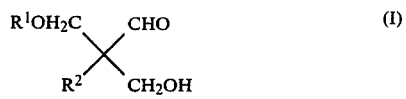

It is stated that these aldols can be converted to the desired ether-malonic acids by a method conventionally used for similar substances, ie. oxidation with nitric acid at as low as 20°–40° C. in the presence of a metal salt of sub-group VII (cf. German Laid-Open Application DOS No. 1,568,227).

To date, it has been possible to obtain ether-malonic acids by only one route, which appears neither economical nor viable from the point of view of safety. According to Ar. 297(4) (1964), 219, monoalkyl-substituted malonates, which themselves are difficult to prepare and therefore not very economically attractive, can be reacted with chloromethyl alkyl ethers, which are known to be toxic and difficult to handle, to give disubstituted alkoxymethyl-allkylmalonates.

For economic and safety reasons it was therefore necessary to find a simple industrial synthesis for substituted ether-malonic acids. On the other hand, the starting materials for a process as proposed in German Laid-Open Application DOS No. 1,568,227, ie. alkoxymethylalkyl-hydroxypropanals, are virtually unobtainable.

Although similar compounds of this type are assumed to occur as intermediates in the formation of ether-alcohols from an alkanol and formaldehyde in the presence of an alcohol and sodium hydroxide solution, ie.

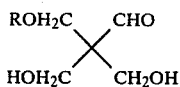

these compounds too have not been described explicitly (Acta Chem. Scand. 25 (1971), 2211).

The corresponding ether-diols, which are likewise suitable starting materials for the preparation of the substituted ether-malonic acids, are also virtually unobtainable since they can be prepared only by reduction of the malonates, which, as stated above, are difficult to obtain (Chim. geterocikl. Soed. 4 (1968), 614), or in a few cases by means of a Cannizzaro reaction in a version which is technically complicated and expensive in terms of materials (Japanese Preliminary Published Application No. 74/025248).

We have found a generally applicable process for the preparation of these substituted ether-aldols, in which a 2-alkylacrolein is reacted with an alcohol (alkanol) and formaldehyde, preferably aqueous formaldehyde, in the presence of a tertiary amine, preferably an alkylamine which has a $pK_B$ above 6, eg. from 9 to 11.

For example, from 1 to 1.5 moles of formaldehyde and, for example, from 4 to 6 moles of the alcohol are employed per mole of 2-alkylacrolein.

The reaction generally proceeds at an adequate velocity and selectivity at from 60° to 100° C. under atmospheric pressure; depending on the compound used, the temperature employed can be from room temperature to 150° C.

Apart from 2-propoxymethyl-2-methyl-hydroxypropanal, which happens to be a known compound, the compounds obtainable by the invention are novel substances which open up an advantageous route to crop protection agents, via appropriately substituted malonic acids or malonates.

The 2-alkylacroleins required are obtainable by Mannich condensation of an n-alkanal with formaldehyde, for example by the method described in German Laid-Open Application DOS No. 3,106,557.

EXAMPLE 1

Preparation of 2-methoxymethyl-2-hydroxymethylpropanal 22 g of triethylamine are added to a mixture of 590 g of methanol, 330 g of 30% strength formaldehyde solution and 210 g of methacrolein in the course of 10 minutes, and the solution is kept at the boiling point for 8 hours. The low-boiling components are separated off, after which 312 g (=78% yield, based on methacrolein) of the title compound of boiling point 120°–125° C./24 mbar are isolated by distillation under reduced pressure.

EXAMPLE 2

Preparation of 2-methoxymethyl-2-hydroxymethylhexanal 37 g of triethylamine are added to a mixture of 550 g of methanol, 500 g of 30% strength formaldehyde solution and 450 g of butylacrolein in the course of 15 minutes, and the mixture is then refluxed for 15 hours. 206 g (35.4%, based on butylacrolein converted) of 2-methoxymethyl-2-hydroxymethylhexanal of boiling point 105°–107° C./3 mbar are obtained by distillation under reduced pressure.

EXAMPLE 3

Preparation of 2-methoxymethyl-2-hydroxymethylbutanal 1280 g of methanol, 500 g of 30% strength formaldehyde solution, 328 g of ethylacrolein and 41 g of triethylamine are reacted as described in Example 1. 390 g (=67% yield, based on ethylacrolein) of the title compound of boiling point 95°–100° C./3 mbar are obtained by distillation under reduced pressure.

USE EXAMPLE 1

Preparation of methoxymethyl-methylmalonic acid 0.1 g of $MnCl_2.H_2O$ is added to 700 g of 65% strength nitric acid ($d^{20}=1.40$), and 300 g of 2-methoxymethyl-2-hydroxymethylpropanal are introduced at 35°–40° C. in the course of 90 minutes. When the reaction is complete, 150 g of water are added, and the mixture is cooled to 0° C., while stirring. The acid which crystallizes out during this procedure is filtered off under suction and is dried.

Yield: 150 g (84%, based on aldol)

Melting point: about 60° C., with decarboxylation

USE EXAMPLE 2

Preparation of methoxymethyl-propylmalonic acid 100 g of 2-methoxymethyl-2-hydroxymethylpentanal are added to a mixture of 356 parts by weight of concentrated $HNO_3$ ($d^{20}=1.40$) and 0.13 g of $MnCl_2.H_2O$ at 35° C. in the course of 60 minutes.

When the solution is cooled to 5° C., 57 g of acid are precipitated in crystalline form.

Yield: 47%, based on aldol

Melting point: 90°–94° C., with decarboxylation

USE EXAMPLE 3

Preparation of methoxymethyl-butylmalonic acid 304 g of $HNO_3$ ($d^{20}=1.40$), 0.1 g of $MnCl_2.H_2O$ and 100 g of 2-methoxymethyl-2-hydroxymethylhexanal are reacted as described in Example 2.

Yield: 83 g (70%, based on aldol)

Melting point: above 100° C. (decarboxylation takes place from 100° C.).

We claim:

1. A process for the preparation of an aldol of the formula (I)

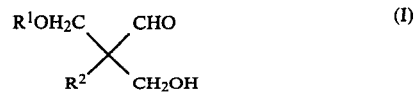

where $R^1$ is a straight-chain or branched alkyl radical of not more than 5 carbon atoms and $R^2$ is a straight-chain or branched alkyl radical of not more than 6 carbon atoms, wherein a corresponding 2-alkylacrolein compound of the formula $H_2C=CR^2-CHO$ with $R^2$ being a straight or branched chain alkyl of not more than 6 carbon atoms, a corresponding alcohol of the formula $R^1OH$ with $R^1$ being a straight or branched alkyl of not more than 5 carbon atoms together with formaldehyde are reacted in the presence of a tertiary amine having a $pK_B$ of from 9 to 11, and wherein from 4–6 moles of said alcohol and from 1 to 1.5 moles of formaldehyde are employed per mole of said 2-alkylacrolein in said reaction.

2. A process as claimed in claim 1, wherein the tertiary amine used is an alkylamine having a $pK_B$ of from 9 to 11.

3. A process as claimed in claim 1, wherein formaldehyde is used in the form of its aqueous solution.

4. An aldol of the formula I

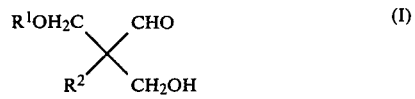

wherein $R^1$ is a straight or branched chain alkyl radical of not more than 5 carbon atoms and $R^2$ is a straight or branched alkyl radical of not more than 6 carbon atoms.

* * * * *